United States Patent [19]

Ross et al.

[11] Patent Number: 4,795,542
[45] Date of Patent: Jan. 3, 1989

[54] ELECTROCHEMICAL CONCENTRATION DETECTOR DEVICE

[75] Inventors: Pepi Ross, Berkely; Marc J. Madou, Palo Alto; Zoila Reyes, Menlo Park; Joel F. Jensen, Palo Alto; Sharon W. Wing, Cupertino; Virginia G. Rimer, Mountain View, all of Calif.

[73] Assignee: St. Jude Medical, Inc., St. Paul, Minn.

[21] Appl. No.: 855,902

[22] Filed: Apr. 24, 1986

[51] Int. Cl.$^4$ ............................................. G01N 27/46
[52] U.S. Cl. ................................ 204/403; 204/1 T; 204/412; 204/415; 204/435; 435/180; 435/817
[58] Field of Search ............... 204/1 T, 403, 412, 415, 204/435; 435/180, 817

[56] References Cited

U.S. PATENT DOCUMENTS

| | | | |
|---|---|---|---|
| 2,805,191 | 9/1957 | Hersch | 204/402 |
| 3,410,778 | 11/1968 | Krasberg | 204/408 |
| 3,539,455 | 11/1970 | Clark | 204/415 |
| 3,655,546 | 4/1972 | Marovich et al. | 204/415 |
| 3,948,745 | 4/1976 | Guilbault et al. | 204/415 |
| 4,100,048 | 7/1978 | Pompei et al. | 204/415 |
| 4,172,770 | 10/1979 | Semersky et al. | 204/412 |
| 4,267,273 | 5/1981 | Smith | 435/817 |
| 4,297,173 | 10/1981 | Hikuma et al. | 204/403 |
| 4,388,166 | 6/1983 | Suzuki et al. | 204/403 |
| 4,525,704 | 6/1985 | Campbell et al. | 204/403 |
| 4,541,901 | 9/1985 | Parker et al. | 204/402 |
| 4,571,192 | 2/1986 | Liu et al. | 204/1 T |
| 4,624,261 | 11/1986 | Holscher | 204/415 |
| 4,627,906 | 12/1986 | Gough | 204/412 |
| 4,655,880 | 4/1987 | Liu | 204/403 |

FOREIGN PATENT DOCUMENTS

1290701 9/1972 United Kingdom.

Primary Examiner—T. Tung
Attorney, Agent, or Firm—James T. Williams; Donald A. Peterson

[57] ABSTRACT

Electrochemical biosensor systems or apparatus, components thereof, and methods for quantitatively measuring or assaying concentrations of selective substrates or metabolites in aqueous media as a function of electrochemical response to hydrogen peroxide concentration, using immobilized enzyme electrode means selective for the substrate or metabolite being measured.

30 Claims, 2 Drawing Sheets

ELECTROCHEMICAL CONCENTRATION DETECTOR DEVICE

BACKGROUND OF THE INVENTION

1. Field Of The Invention

This invention relates to a concentration detector device containing a set of electrodes and a composite membrane structure wherein an enzyme, specific to a substance found in a fluid sample, is immobilized. The concentration of the substance found in the fluid sample is determined by proportional comparison with the amount of current generated from the oxidation of the product of an enzymatic reaction at the anode of the detector device. This invention also relates to methods for determining the concentration of glucose or other substrates in blood, body fluids and other solutions using this detector device.

2. Description Of The Prior Art

For medical and research purposes it is often important to accurately and rapidly measure the concentration of certain substances found in body fluids, such as glucose. For example, it is critically important to rapidly and accurately monitor blood glucose levels in diabetic patients who require injections or infusions of appropriate dosage levels of insulin to control blood glucose levels. Additionally, blood glucose determinations can be important when a diabetic patient is acutely ill, undergoing surgery or childbirth or suffering from severe keto-acidosis.

The prior art describes a number of detector devices for electrolytically analyzing the concentration of a substrate by measuring electrically the components produced by reaction of an enzyme specific to a substrate contained in a sample.

For example, Clark U.S. Pat. No. 3,539,455 describes a device and system wherein glucose, in a body fluid sample, is oxidized by glucose oxidase to convert the same to gluconic acid and hydrogen peroxide, the latter being detected polarographically. Other interfering materials in the sample which result in extraneous currents according to Clark are compensated for by current subtraction.

Newman, U.S. Pat. No. 3,979,274 (1976) discloses a system where a membrane laminate contains glucose oxidase enzyme in an adhesive layer in close proximity to a reference electrode.

Wilkins, U.S. Pat. No. 4,440,175 (1984) describes a implantable electrode which includes a membrane formed on a conductive substrate, the membrane containing a polymeric anion exchange species with a water soluble salt of the nonionic species to be measured. The device is used to measure glucose concentration in vivo.

Shichiri et al., "Wearable Artificial Endocrine Pancreas With Needle Type Glucose Sensor", Lancet, Nov. 20, 1982, pp. 1129-31, describes an implantable needle electrode for monitoring glucose which has at the end a urethane ball structure containing immobilized glucose oxidase (in cellulose-diacetate with a heparin anticlotting agent) surrounding a platinum electrode (anode) and a silver cathode "body" surrounding the anode and separated therefrom by a glass wall or tube.

The present detector device incorporates several design features which permit quick determinations of substrate concentration more accurately and reliably than the prior art. Particularly, the detector device of the present invention can be used to accurately and reliably measure the concentration of glucose in solution.

To measure glucose concentration the enzyme glucose oxidase is immobilized within a detector cell near a set of planar electrodes. A solution containing glucose is deposited in the detector device cell. The immobilized enzyme, glucose oxidase (GO) causes the catalysis of glucose to gluconic acid and hydrogen peroxide in accordance with the general Reaction (1), below:

This reaction is described in Reed, G. Enzymes in Food Processing, Academic Press, NY (1975), p. 231 as follows:

The enzyme glucose oxidase (termed E-FAD in the above reaction) is said to extract two hydrogens from $\beta$-D-glucose to form the reduced enzyme, EFADH$_2$ and the gluconic acid lactone. The lactone hydrolyzes in the presence of water to gluconic acid (nonenzymatically) and the reduced enzyme E-FADH$_2$ is reoxidized by molecular oxygen to E-FAD.

The resulting hydrogen peroxide produced as shown in reaction 1-A is then oxidized at the Pt electrode held between +0.7 to +0.9 volts in order to produce electrons and current, as shown in Reaction (2) below:

The current generated in Reaction (2) is thus directly proportional to the concentration of glucose found in the sample which is deposited in the detector device cell, provided there is sufficient oxygen to carry out the regeneration step in Reaction (1-A). A source of oxygen can also be provided to facilitate the regeneration of glucose oxidase according to Reaction (1-A).

The generating of available oxygen in the reaction volume present in the sample cup or reservoir by the electrolysis of water offers significant operational advantages to the detector system of this invention. It is noted that in situ generation of oxygen by the electrolysis of water is discussed by Enfors in Enzyme Microb Technol., 3, 29-32 (1981) with respect to investigative efforts to develop a regeneratable glucose oxidase electrode which could be used to continuously measure the concentration of glucose of a fermentation broth.

SUMMARY OF THE PRESENT INVENTION

It is an object of the present invention to provide a concentration detector device which comprises a set of electrodes and a composite membrane structure containing an immobilized enzyme. More specifically, it is an object to provide a detector device to determine the concentration of glucose by measurement of the amount of current generated from the oxidation of hydrogen peroxide produced by the catalytic oxidation of glucose in a sample of given volume at an electrode contained in the detector device.

It is also an object of this invention to provide a detector device with design features which permits quick determinations of selected substrate concentration more accurate and reliable.

More particularly, it is a further object of this invention to provide an electrochemical detector device with planar electrodes which provide for enhanced reproducibility and uniformity of calibration.

It is a still further object of this invention to provide an improved, permeable, flexible and resilient membrane structure used in the detector device for the immobilization of an enzyme. This membrane structure also allows for the rapid diffusion therethrough of the substrate and the peroxide reaction product of the enzymatic reaction with the substrate, to the planar electrodes.

These and other objects of the invention will be apparent hereinafter from the specification. Reference should also be made to the attached drawings, and the appended claimed.

Generally, the objects of this invention are accomplished by a concentration detector device which includes three functional elements and an associated reservoir adapted to contain a predetermined amount of fluid sample containing a substrate to be measured in operational contact with the sample to be analyzed.

The first element comprises a group of three flat or planar electrodes each deposited as an adherent film on a flat or planar nonconductive mechanical base surface.

The second element comprises a permeable inner membrane made from a water insoluble polymer chemically bound to an enzyme to immobilize the same.

The third element comprises a permeable polymer membrane disposed between the sample and the inner membrane which provides a biocompatible interface with body fluids bearing the substrate in question and has pore sizes which result in exclusion of interfering components of a sample undergoing test from the substrate being analyzed by enzymatic oxidation in the inner membrane.

A further electrode is provided which is adapted to contact the sample contained in the reservoir and complete the associated electric circuit for the generation of oxygen at one of the planar electrodes by the electrolysis of water in regeneration of the enzyme. The total assembly comprises an electrolytic assay cell.

The detector device of this invention involves the use of planar electrodes for quantitatively determining hydrogen peroxide concentration. The planar electrodes contemplated in this invention have flat, predetermined and readily reproducible variable shapes or configurations and sizes. The planar electrodes of this invention may be adherently and securely attached by selected means on a surface such as a nonconductive or insulative supporting structure or base surface such as a planar glass slide or a plastic bar, such as Mylar TM, in the form of an adherent film of desired thickness. The planar character of the electrodes significantly enhances the reproducibility and uniformity of end results and ease of calibration as compared to other forms, since signal amplitude of the device is a function of surface area of the sensing electrode.

Thus, in determining or assaying the glucose concentration in whole blood samples using the devices of this invention, the planar hydrogen peroxide detector electrode assembly, when held at an appropriate constant applied voltage, senses and signals the presence and concentration of hydrogen peroxide by quantitatively sensing the electrons or current generated by Reaction (2), above. A constant applied voltage ($E_A$) of between +0.7 to +0.9 volts is required for this amperometric system. Stated differently, by holding the applied voltage at between +0.7 to +0.9 volts, the $H_2O_2$ is oxidized at a polarized planar nonreactive electrode such as platinum. Although a planar Pt electrode is preferred, one may also use, with modification, other planar electrodes formed, for example, of gold, carbon, or nickel or an alloy thereof. For convenience, the chemical symbols for platinum and silver/silver chloride are used in place of their common chemical names. Additionally, electrodes, made from a mixture of carbon and a metal, may be used, e.g., 95% carbon and 5% Pt. The resultant current is sensed quantitatively, thereby precisely signaling the $H_2O_2$ concentration in terms of current. It is important to note here that very few other compounds are oxidized at such a low voltage. For this reason, the procedure operated at an applied voltage of between +0.7 and +0.9 volts, and preferable at +0.8 volt becomes essentially selective for peroxide and there is minimal opportunity for interference from other components of the sample.

This invention includes as one embodiment thereof the manufacture and use of an improved, fluid permeable polymeric membrane containing therein an immobilized enzyme selected for and specific to a particular substrate or metabolite to be measured or assayed in the aqueous body fluid sample.

The enzyme(s) is preferably uniformly distributed in situ substantially throughout the inner membrane layer. The enzyme(s) is covalently or chemically bound to and in the polymeric material used to form the inner layer membrane, to thereby provide prolonged and uniform retention of immobilized enzyme(s) in an active and substantially stabilized state. To the extent understood, it is believed that the inner membrane thus has distributed therein supported sites of active, immobilized, covalently bound enzyme(s) specific to or selective for the substrate(s) in the sample being measured or assayed for that specific substrate. Furthermore, the immobilized enzyme resists being leached from the inner membrane for a prolonged period of time (e.g., up to 12 weeks), and within its useful life, provides reliable and reproducible results in a cell device.

As previously indicated the inner permeable membrane comprises a water-insoluble polymeric matrix to which an enzyme is covalently bound. Enzymes, in general, are water soluble, and frequently very unstable substances. In nature, enzymes are frequently attached to cell surfaces or entrapped in cell membranes. An immobilized enzyme has been found to provide the most stable, economic and efficient means for the use of an enzyme in the context of this invention.

In the present invention the enzyme glucose oxidase can be immobilized by covalently bonding the anhydride group of poly(styrene-maleic anhydride) copolymers (SMA) to amine groups found in the enzyme glucose oxidase. In the prior art, glucose oxidase has been covalently bound to a supporting polymer through the use of glutaraldehyde as a linking agent between the enzyme and the polymer. In the present invention, however, no special reagents such as glutaraldehyde are needed, thereby eliminating the drawbacks associated with the use of that material. The reaction can be carried out by simply dispersing or emulsifying an aqueous solution of the enzyme in an organic solvent solution of the polymer and allowing the reaction to take place which proceeds at room temperature in a period of a few hours. This results in a polymer containining the immobilized glucose oxidase enzyme—here sometimes referred to as SMA-GO. The activity of the glucose oxidase enzyme, or its capacity to be regenerated from its reduced form by oxygen, is found not to be significantly affected by immobilization.

This enzyme membrane film has been found to be stabilized by adding polyvinyl acetate to the resin before membrane or film formation. It has been found that conventional SMA films are brittle and crack easily. Similarly, when glucose oxidase is reacted with the SMA polymer, the films cast from the product can also crack. To prevent this, a plasticizing binder such as polyvinyl acetate is used to impart mechanical stability and flexibility or resilience to the films or membranes and also improve their adhesion to the planar electrodes and the other permeable membrane.

Polyvinyl acetate modified SMA-GO resins, however, are not as permeable to water as the unmodified SMA-GO resins and response time becomes very slow in cells using unmodified polyvinyl acetate containing SMA-GO films. It has been discovered, however, that the incorporation of polyethylene glycol (600) in conjunction with the enzyme and the polyvinyl acetate into the SMA resin can improve the permeability of films or membranes cast from the resulting compositions.

Preferably, the modified SMA-GO membrane overlies and covers the supported planar electrodes of the device. The inner enzyme membrane layer is thus in substantially interfacial contact with the planar electrodes formed on the base surface (e.g., electrodes and membrane are separated by a capillary distance or less). Particularly effective results are obtained when the inner membrane is proximally cast in intimate contact with the supported planar electrodes, so that the membrane lies on the surface of the electrodes.

In addition to the SMA-GO inner membrane, a second outer permeable membrane layer is provided which has an outer biocompatible surface which is in contact with and receives the sample to be chemically analyzed and contained in the reservoir. The outer membrane has micropores which are too small to destroy blood compatibility, or result in coagulation of blood, but are large enough to allow for the rapid diffusion therethrough of the substrate (e.g., glucose) in the sample to be assayed. Moreover, it is important that the micropores formed in the outer membrane be of such a size as to limit the passage of any interfering material in the sample (e.g., ascorbic acid, acetaminophen, or peroxidase), which could be oxidized by the Pt electrode and thus generate current and give a false reading.

The inner SMA-GO membrane and outer permeable membrane together form a composite membrane or assembly, which composite structure may be shaped to different configurations, and are positioned in substantially interfacial contact to, or in intimate contact with each other. Particularly effective results are obtained by casting the inner immobilized enzyme-containing membrane layer directly over the supported planar electrodes and allowing that formed-in-place membrane to harden (e.g., air-dry), and then casting the outer microporous layer onto the hardened inner layer and then allowing the outer formed-in-place layer, in turn, to harden, to provide an integral, layered composite membrane structure or assembly in which the inner and outer membrane layers are securely affixed to each other and to the planar electrodes. The inner membrane can also be silk screened over the planar electrodes. In one preferred embodiment the assembly of planar electrodes and composite membranes are flat with an approximate height of up to about 3 mm.

The structural integrity of the operative membrane composite in the detector device may be protected by physically placing and retaining an inert, biocompatible (e.g., blood-compatible), permeable mesh-like material or fabric (e.g., with pores) directly on top surface of the otherwise exposed outer surface of the outer membrane.

The detector device of this invention may also include an auxiliary oxygen-generating electrode means, which can be used to generate oxygen in situ (by effecting the electrolysis of available water present in the sample) at the locus of an oxygen-generating electrode positioned on the support base under the immobilized enzyme (SMA-GO) membrane.

For example, in assaying the concentration of hydrogen peroxide produced enzymatically from glucose in blood, free oxygen must be present or available in the aqueous fluid sample being assayed to participate in the catalytic reaction. (See equation 1-A) supra. In whole blood samples for example, much, if not most, of the oxygen is bound to hemoglobin and is thus not available for participation in the reaction. This problem has been a barrier to the proper operation of various blood glucose sensors, which depend on the enzymatic generation of hydrogen peroxide from glucose in whole blood samples. The oxygen-generating electrode means of this invention produces oxygen in situ by the electrolysis of water present in the sample, such as whole blood, to be tested.

Further advantages of the invention are apparent from the following description, including accompanying drawings, of illustrative embodiments of the invention.

BRIEF DESCRIPTION OF THE DRAWINGS

For a more complete understanding of this invention, reference should be made to the drawings, in which.

DESCRIPTION OF THE PREFERRED EMBODIMENT

Figure 1:
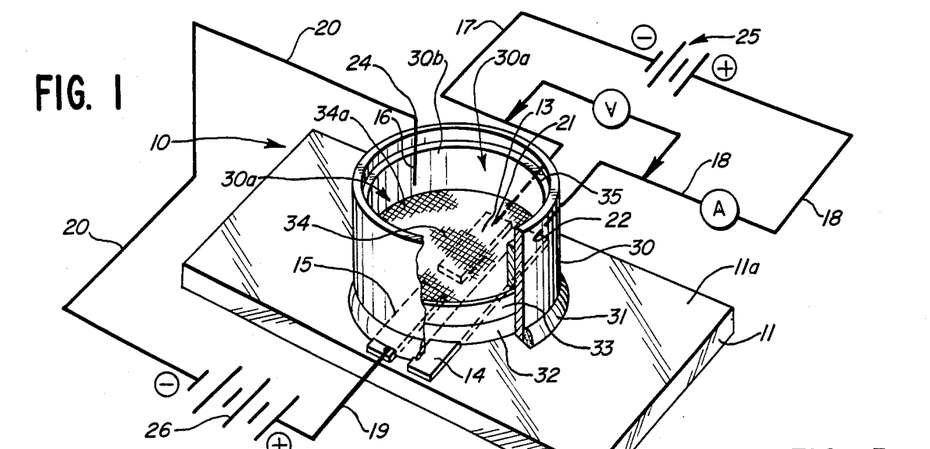
FIG. 1 is a perspective view in partial section of one embodiment of the electrochemical concentration detector device of the present invention and associated circuitry for its operation.

Referring to the drawings, FIG. 1 shows in perspective an embodiment of the electrochemical concentration detector device 10 for the amperometric, quantitative measurement of hydrogen peroxide generated by the enzymatic catalysis of a substrate.

Figure 2:
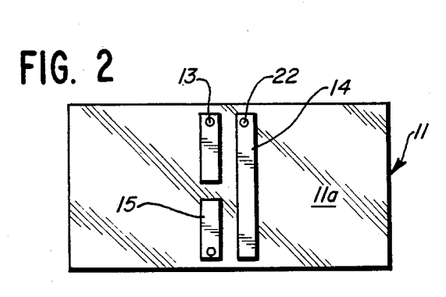
FIG. 2 is a top plan view of the base surface 11 of the device 10 shown in FIG. 1 showing planar electrodes affixed to the surface thereof.

The electrochemical assay device 10 comprises an electrically nonconductive planar supporting means or base surface 11, which, in the illustrated embodiment is a conventional laboratory glass slide. The base may also be formed of other nonconductive materials such as Kevlar TM, Mylar TM or the like. In FIG. 2, two planar platinum (Pt) electrodes 14 and 15, and a planar silver/silver chloride electrode 13 are shown formed on the top surface 11a of the base 11. A silver electrode located at 13 is formed by deposition of silver on surface 11a and the silver is chloridized to form an adherent planar Ag/AgCl electrode 13 for electrochemical purposes, without affecting its silver-to-glass bond to the top surface 11a of base 11. The planar electrodes 13, 14 and 15 are adherently and securely deposited on the top surface 11a of supporting means 11 by any of several known means, such as vacuum deposition, including sputtering (under vacuum), silk screening and electrolytic processes. Die cut electrodes of thin sheet form may also be adhered to the support base, although this is not preferred.

Figure 3:
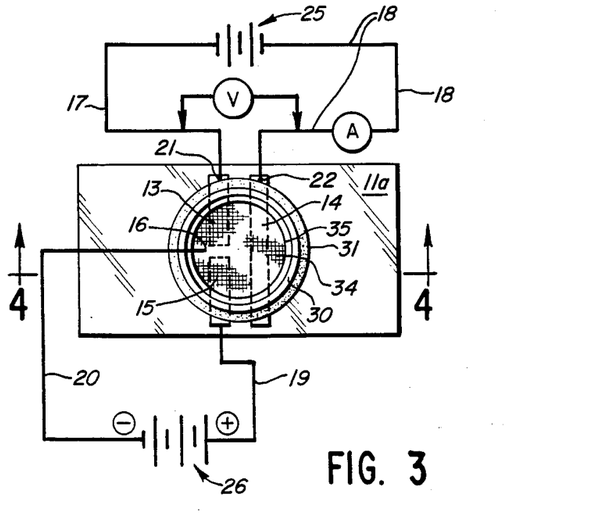
FIG. 3 is a top plan view, of the device of FIG. 1.
Figure 4:
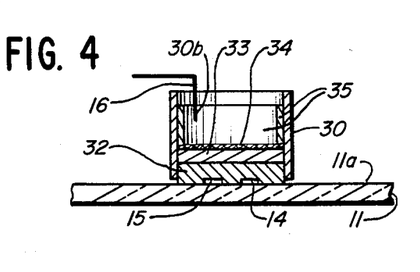
FIG. 4 is a vertical sectional view of the detector device of FIG. 3 taken along the lines 4—4.

A nonconductive reservoir cup or cavity 30a of the device 10 is formed by centering one open end of a tube in the embodiment shown, of a generally cylindrical ceramic ring 30 of predetermined standard size and shape to the top surface 11a of the base 11 about the planar electrodes 13, 14 and 15 and securing the same by cement or adhesive 31 which may be a curable epoxy or silicone cement, as shown in FIGS. 1, 3 and 4.

The planar electrodes 13, 14 and 15 are overlaid by a permeable, layered, composite membrane structure (32 and 33) which are in intimate contact with each other and which allow the components of a fluid sample contained in the cavity 30a of the cup 30 to diffuse therethrough free or essentially free of interfering material or substances.

The inner permeable membrane 32 comprises a poly(styrene-maleic anhydride) [SMA] polymer containing the immobilized glucose oxidase enzyme which is evenly distributed and chemically or covalently bound to the anhydride group thereof to produce the so called SMA-GO resin. Membrane 32 has micropores formed therein to permit the flow of liquid or fluid sample therethrough. The inner SMA-GO membrane 32 is a contact-reaction element that enzymatically converts a substrate such as glucose to gluconic acid and hydrogen peroxide. Hydrogen peroxide is oxidized at detector electrode 14; this electrode is maintained at a potential of from between +0.7 to +0.9 volts with respect to electrode 13.

The planar Pt electrode 15 (in conjunction with electrode 16 of platinum wire) generates oxygen by the electrolytic decomposition of water contained in a sample placed in cup 30. Oxygen so generated at electrode 15 diffuses into and through the inner membrane 32 to participate in the glucose oxidase catalyzed reaction. The inner membrane 32, (SMA-GO) is in close interfacial contact with the planar electrodes 13, 14 and 15, readily secured by casting a layer of the resin thereover.

The outer permeable membrane 33 overlies membrane 32 and also has micropores formed therein and is blood-compatible. Membrane 33, however limits or largely restricts the passage of interfering materials or compounds to the inner membrane while, at the same time, in the case of glucose analysis, allowing glucose from a blood sample, to rapidly diffuse therethrough.

FIGS. 1 and 4 illustrate a protective means 34, for imparting added structural integrity or mechanical protection to the membranes and detector device. In the embodiment shown the means 34 is an inert, blood-compatible cloth, polymeric mesh or screen having a plurality of small liquid permeable apertures which overlies and directly contacts the outer face of membrane 33. Means 34 is securely retained, at its periphery, against the outer membrane by means of an nonconductive retention ring or sleeve 35 that is frictionally and securely snap-fitted into place in the cavity 30a of reservoir ring 30 as shown in FIG. 1.

Figures 5, 6:
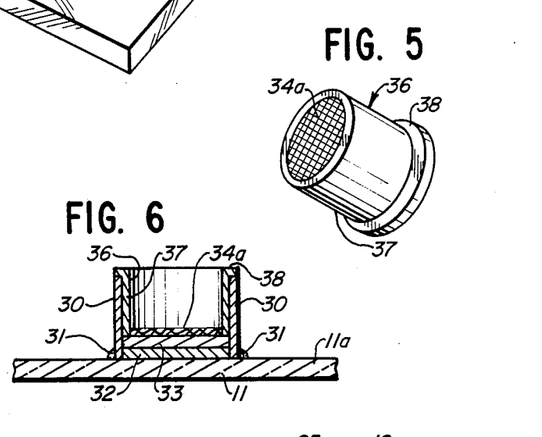
FIG. 5 is a persective of an alternative form of a mesh-retaining assembly useful in the device of FIG. 1.
FIG. 6 is a vertical sectional view of the screen assembly shown in FIG. 5, taken along the lines 6—6.
Figure 7:
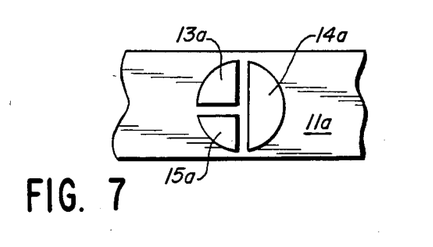
FIG. 7 is a top plan view of an alternative form showing semi-circular planar electrodes formed on a base surface.
Figure 8:
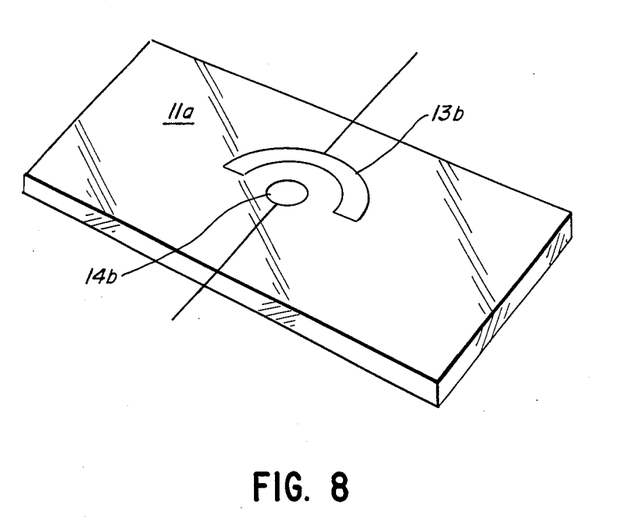
FIG. 8 is a top plan view of an alternative form of the platinum-silver/silver chloride electrode pair with a lock and key configuration.

FIGS. 5 and 6 illustrate an alternative form or embodiment of means 34 comprising a thimble-like screen device 36, having a cylindrical or tubular wall 37 and an integrally formed gauze-like or mesh surface 34a across one end thereof to form the said thimble-like structure. A circumferentially extending ring 38 is shown formed at the other end of the wall 37. FIG. 6 shows the unit of FIG. 5 in place inside reservoir 30, replacing the combination of protective means 34 and retaining ring 35 shown in FIGS. 1, 3 and 4. It is easily removed for cleaning and replacement. FIG. 7 is an illustration of an alternative embodiment using three planar circular sector electrodes 13a, 14a and 15a. FIG. 8 is a further alternative embodiment illustrating only the platinum (14b)-silver/silver chloride electrode pair. The configuration has the advantage of reducing impedance which is particularly important when more than two electrodes (not illustrated in FIG. 8) are used. A further embodiment, not illustrated, is a unit employing four planar electrodes wherein electrode wire 16 is also a planar electrode affixed to the base surface 11a.

The shaped, permeable, outer membrane layer 33 is biocompatible (e.g., blood-compatible) with samples containing the substrate or metabolite to be assayed in aqueous media. A liquid sample containing a substrate to be analyzed, such as glucose in blood, flows through mesh 34, to outer membrane 33 which allows the substrate to rapidly diffuse therethrough to the inner membrane 32 while, at the same time, providing a barrier which selectively restricts or limits the passage therethrough of undesired, interfering material or substances, including, but not limited to, particles and high molecular weight materials or substances, present in the aqueous sample being assayed, which would react with and affect the selectivity of response of the electrochemical, quantitative hydrogen peroxide detector electrode 14. In the preferred embodiment the outer membrane 33 may be formed, for example, of a polyurethane resin.

It is preferable that the inner membrane 32 and outer membrane 33 be positioned in interfacial contact with each other or bonded together, since such interface contact provides a short flow pathway limiting interfering material or substances, gives mechanical strength and also provides the desired rapid response time for $H_2O_2$ detection. However, it has been found that membranes 32 and 33 could be positioned in spaced relationship to each other, provided they were in operative coacting proximity to, or in the operative coacting vicinity of each other. In use, the aqueous substrate fills such limited space so as to maintain a continuous electrical pathway between the oxygen-generating electrode pair 15 and 16.

As shown in FIGS. 1, 3 and 4, a Pt wire electrode 16 vertically extends into the sample contained in the reservoir cup 30 at a level indicated at 30b into a substrate or metabolite sample container therein, but does not contact the surface of either the outer membrane 33 or overlying cloth membrane 34 as shown in FIGS. 1 and 4.

The continuous electrical pathway between the planar Pt anode electrode 14 and planar Ag/AgCl electrode 13 is maintained by the sample functioning as an electrolyte, which contacts those electrodes. Likewise, the continuous electrical pathway between the oxygen-generating electrode pair 15 and 16 is operatively maintained by the sample acting as an electrolyte.

FIGS. 1 and 3 illustrate the electrical circuitry used to apply a constant voltage of 0.8 volt to the pairs of electrodes 13 and 14 to measure peroxide generation, and the electrolysis voltage to electrodes 15 and 16.

The electrical circuitry used to measure the electrochemical oxidation of Reaction (2), and amperometrically measure the current produced by that process comprises application of a predetermined, fixed or constant voltage of +0.8 volt across the electrode pair 13 and 14. Conductor or wire 18 connects the positive terminal of the battery 25 to the planar working Pt electrode 14 at 22, and conduit or wire 17 connects the negative terminal of the battery 25 to the planar Ag-/AgCl reference electrode 13 at 21. Accordingly, the planar platinum working electrode or anode 14, at which the hydrogen peroxide is oxidized is positive whereas the planar Ag/AgCl reference electrode 13 is negative. A voltmeter V is shown positioned across the wires 17 and 18, and an ammeter A is shown positioned in the circuit of conduit or wire 18. In testing for levels of blood glucose, a constant applied voltage ($E_A$) of +0.8 volt from the source is maintained and $H_2O_2$ is generated by catalysis, and the corresponding current flow is measured by ammeter A, thereby determining $H_2O_2$ concentration in terms of current flow. [See Reaction (2)]

FIGS. 1 and 3 also show the electrical circuitry used for electrolysis of water across electrodes 15 and 16 to generate oxygen, in situ which is used to regenerate the immobilized enzyme. Connecting wire 20 connects the negative terminal of the battery 26 to the overhanging, vertically extending Pt wire electrode 16 (at 24), and wire 19 connects the positive terminal of the battery 26 to Pt electrode 15. Hydrogen formed from the electrolysis of water present in the sample of blood is generated at the Pt electrode 16 and oxygen is generated at the Pt electrode 15. Oxygen is thus provided and diffuses into the inner membrane 32 in the zone where Reaction (1-A), above, occurs. In the case of whole blood samples, a constant applied voltage ($E_A$) of from +3 to 4.5 volts is used to produce oxygen for regeneration of the catalyst glucose oxidase.

In calibrating the device or assembly 10, saline solutions may be prepared having different known concentrations of glucose (i.e., mg./100 ml.) and the current generated at an $E_A$ of +0.8 volt plotted against the glucose concentration, thereby obtaining the relationship or correlation between the concentration of glucose in a liquid sample and the oxidation current signaled at +0.8 volt. Thus in operation when a few drops of a glucose-containing sample are inserted into the cavity 30a of sample cup or reservoir 30 and a constant $E_A$ of +0.8 volt is applied, one may readily, accurately, and repeatedly determine the concentration of glucose therein by measuring the current generated by the oxidation of $H_2O_2$ enzymatically formed from glucose in the predetermined volume of sample being assayed.

The following examples will illustrate the formation, assembly and use of the various elements of the illustrated embodiments.

EXAMPLE 1

In forming the illustrative electrode or biosensor assembly shown in the accompanying drawings, the thin, flat or planar electrodes are deposited in the form of an adherent film by either vacuum evaporation or vacuum sputtering. Both processes involve depositing a metal vapor on a surface in a vacuum chamber. The metal to be deposited is removed from a source or target (the cathode), in the form of a plasma and deposited through a mask of predetermined shape defined by an object or surface (at the anode) and bonded thereto by means of a chemical or metallic bond or a van der Waals interaction as in the case of a surface such as that of a lightly sand-blasted laboratory glass slide to provide firmly adhering electrodes covering a predetermined surface area having a thin, flat or planar configuration. (See FIG. 2). This allows the surface area of the flat electrodes to be identical for all detector devices, so that a given concentration of $H_2O_2$ will yield the same current, and thus be a reliable measure of substrate, i.e., glucose concentration.

Experience indicates that the electrode response is relatively independent of the distance separating the Ag/AgCl and Pt electrodes 13 and 14, respectively, as shown in FIG. 1. Furthermore, a simple alternate electrode configuration of partial-circles 13a, 14a and 15a may be used to maximize electrode surface, as shown in FIG. 7. This partial or semi-circular electrode configuration maximizes the surface area (and thus the signal) for the size of unit chosen.

In forming one specific embodiment of electrodes, one side of flat glass sides (3 in.×1 in.×0.05 in.) are sand-blasted to a dull finish using an air abrasion unit (Model F, S.S. White Maesner) using 25-micron alumina grit. The glass slide is then cleaned with a conventional cleaning solution, such as Micros TM liquid laboratory cleaner, a product of International Products Corp., and deionized water in a heavy duty ultrasonic cleaner (e.g., Model DS 850A of Delta Sonics) for 10 minutes, after which the slides are rinsed for 30 min. with flowing deionized water. The slides are blow-dried with nitrogen.

When the electrodes are deposited by sputtering rather than by evaporation two glass slides are loaded in a mask holder for platinum (Pt) deposition and the loaded mask holder is placed in a sputtering unit (e.g., Model V4 MRC RF sputtering unit) which is operated in $10^{-6}$ Torr vacuum.

In the first deposition run, a thin layer of chromium (Cr) is first deposited on the sand-blasted glass surface to enhance adhesion, followed by the deposition of the two platinum (Pt) electrodes thereover. The deposition sequence and conditions shown in Table A, below:

TABLE A

| Deposition Run | Time | Watts of Radio Frequency Power |
|---|---|---|
| Plasma-clean sample | 2 min. | 150 W RF Power |
| Pre-sputter Cr target | 5 min. | 300 W RF Power |
| Sputter Cr | 50 sec. | 150 W RF Power |
| Pre-sputter Pt target | 1 min. | 150 W RF Power |
| Sputter Pt | 30 min. | 200 W RF Power |

TABLE A-continued

| Deposition Run | Time | Watts of Radio Frequency Power |
| --- | --- | --- |
| $R_s$ (sheet resistance) = 1 ohm | | |

The vacuum station is opened, the glass slides are repositioned in the mask holder for silver (Ag) deposition, and the sputtering unit is again pumped to $10^{-6}$ Torr vacuum. Again, chromium (Cr) is first deposited on the sand-blasted surface to provide improved adhesion. The deposition sequence conditions for the silver electrode are shown in Table B, below:

TABLE B

| Deposition Run | Time | Watts of Radio Frequency Power |
| --- | --- | --- |
| Plasma-clean sample | 2 min. | 150 W RF Power |
| Pre-sputter Cr target | 5 min. | 300 W RF Power |
| Sputter Cr | 50 sec. | 150 W RF Power |
| Pre-sputter Ag target | 1 min. | 150 W RF Power |
| Sputter Ag | 35 min. | 150 W RF Power |
| $R_s$ (sheet resistance) = 0.1 ohm | | |

EXAMPLE 2

Identical inert, electrically nonconductive, vertically extending cylindrical ring or reservoirs (30) of constant size and shape are accurately and identically centered about the planar electrode assembly formed in Example 1, above, and secured to each of the glass slides. The rings may be formed of and cut from, for example, ceramic material [e.g., AD-99 mullite, high alumina, Coors porcelain tubes and insulators having a single bore and open ends with a constant outside dia. of 0.375 in. and a constant inside dia. of 0.250 in., (Catalogue No. 65660); supplied by Technical Distributors, Inc.].

More particularly, the bottom of each vertically extending ceramic ring is securely tacked onto the electrode surface of the glass slide, for example, by placing spaced-apart drops of adhesive, such as an epoxy resin (e.g., Epoxi-Patch Kit TM, IC White, of the Hysol Division, The Dexter Corp.) to the bottom (abutting) annular surface of the ring to the glass slide. The outer end of each of the three planar electrodes extends a short distance beyond the outer periphery of the ceramic ring at the base of the ring. The entire lower, abutting outer periphery of the ring is sealed (at 31) with the same epoxy adhesive material after the electrical lead wires are connected, as described below, to provide a firmly secured and sealed sample ring or reservoir. The sealing epoxy adhesive is cured overnight at room temperature, to prevent cracking.

After tacking the bottom of the ceramic ring in place, but before sealing it to the glass slide, one end of three electrical lead or connecting wires is connected or attached to the outer end of each of the two planar Pt electrodes (14 and 15) and to one of the outer ends of a planar Ag electrode shown and located as reference numeral 13. As explained above, those outer ends of the flat electrodes extend a short distance beyond the outer periphery of the base of the ceramic ring. The electrical lead wires are attached to the respective planar electrodes, for example, by means of a conductive silver-epoxy resin adhesive (e.g., Cho-Bond TM 581-29, a highly conductive, curable adhesive system of Chomerics shielding having fine particle, platelet-type pure silver filler and a curable hardener, but no solvent) that is approximately cured (e.g., at 90° C. for 30 min.).

After sealing the abutting periphery of the ceramic ring to the glass slide, an insulative sample cup or reservoir is formed by the supporting substrate and ring (see FIG. 3).

EXAMPLE 3

(Ag/AgCl Electrode Formation)

The silver (Ag) electrode located as shown by reference numeral 13 formed in Example 1, above, is chloridized to provide a planar Ag/AgCl electrode (13), which enables this electrode to complete the electrical pathway (with electrode 14) and to maintain constant interaction with the sample solution. It is important to form adequate silver chloride (AgCl) in this operation so that the electrochemical Reaction (2), above is never restricted or limited by the reaction process at the reference electrode. In conducting chloridization, a 1M solution of hydrochloric acid (HCl) is prepared. The area of the Ag electrode is determined. The current density for chloridization should be approximately 1 milliamp./cm.$^2$ The electrode is then polarized in HCl at a constant current of approximately 1 milliamp./cm.$^2$ The potential is monitored from an initial value of approximately +0.3 volt until chloridization is completed when the potential has increased to approximately +0.8 volt.

The confines of the sample ring or reservoir is filled with the HCl solution. The Ag/AgCl electrode (13) of the detector device is connected to the working electrode 14 through the battery or potentiostat (26). The working electrode 14 is positive with respect to the reference electrode 13.

The assembled cell is preferably stored in a buffered physiologic saline solution (pH about 7). The silver chloride coating on the Ag/AgCl electrode can also be regenerated or replenished by applying a low voltage more positive than the formal potential of the Ag/AgCl electrode (e.g., typically using 0.8 V, which is convenient because the value is the same as that for the sensing electrode) across the working platinum (14) and Ag/AgCl (13) electrode pair in a saline solution. Alternatively a constant current of about 1 milliamp./cm.$^2$ could be applied. This reaction lends itself to in situ replenishing of the silver chloride electrode in special situations, such as the implantation in mammals.

EXAMPLE 4

(Immobilized Membrane Preparation)

The resin used for the permeable inner membrane is made as follows. A 10% by weight aqueous emulsion of poly (vinyl acetate) [PVAC] is made from an aqueous emulsion of polyvinyl acetate [e.g., VINAC 881 emulsion, a polyvinyl acetate latex product of Air Products and Chemicals, Inc. having 48% minimum solids, a pH of 5 to 6.5, an emulsion viscosity of 50–300 cps. (Brookfield Viscometer, Model LVF, 60 rpm. at 23° C.), and a density of 9 lbs./gal. at 73° F.] in deionized water. Fifty (50) microliters of the resultant 10% weight solution is mixed with 25 microliters of distilled water, and 10 milligrams of glucose oxidase (e.g., G 8135, 100,000 units/g., of Sigma Chemical Co.) are dissolved in the mixture to provide solutions "A".

A 10% (w:v) solution (10 grams of copolymer per 100 ml. of methyl ethyl ketone) of poly(styrene-maleic anhydride) copolymer resin (e.g., No. 3106 of Poly Sciences, Inc. containing 50% by weight of styrene and, having a molecular weight of 1600) in methyl ethyl ketone is prepared, to provide solution "B".

A 20% solution (w:v) of poly(ethylene glycol) (e.g., having an average molecular weight of 600) in methyl ethyl ketone is prepared, to provide solution "C".

125 Microliters of Solution "B" are added slowly with agitation to Solution "A" and the mixture is homogenized in a Vortex homogenizer. 25 Microliters of Solution "C" and 25 microliters of deionized water are added slowly with vortexing to produce a homogeneous emulsion. 25 Microliters of deionized water are added one drop at a time and with vortexing between each addition. The resultant product is diluted with an equal volume of methyl ethyl ketone, added dropwise and then mixed in the vortex.

The resultant diluted emulsion is shaken in a mechanical shaker (e.g., Burrel Wrist Action Shaker at a setting of "7" to provide, for example, about 122 rpm.) for two hours at room temperature to form the final flowable resinous emulsion.

25 Microliters of the resultant emulsion is placed within the confines of the ring. The membrane is allowed to air-dry. The air-dried membrane is then over-cast with 5 microliters of resin solution "D", and the over-cast resin is allowed to air-dry. In forming solution "D," which is later used for over-casting, five parts by weight of the poly(styrene-maleic anhydride) copolymer are dissolved in 95 parts by weight of anhydrous acetone.

It is important to note that: the emulsion and resultant inner membrane is stabilized by action of the polyvinyl acetate in the aqueous emulsion; and the poly(ethylene glycol) sustains the permeability of the inner membrane and later aids in securely bonding the inner membrane to the outer membrane.

EXAMPLE 5

(The Inner and Outer Membranes)

The permeable inner membrane 32 formed-in-place or cast as described in Example 4, above, is covered with a permeable biocompatible resinous outer membrane (33) having a microporous structure. The resin used to form the outer membrane is prepared with 2 parts by weight of a medical-grade, thermoplastic aliphatic polyurethane resin (e.g., Tecoflex TM SG-93 A, a solution grade polyurethane resin of Thermedics Inc. having a hardness of 93 Shore A). The polyurethane resin is formed by reacting methylene bis(cyclohexyl) diisocyanate with polytretramethylene ether glycol in the absence of solvent, and then reacting the reaction product with 1,4-butadiene) and 1 part by weight of poly(ethylene glycol) (e.g., having a molecular weight of 600).

A blood-compatible outer membrane is formed with micropores which are too small to destroy blood-compatibility, but are large enough to allow rapid diffusion therethrough of the sample (e.g., glucose-containing aqueous solutions, such as whole blood) essentially freed of interfering material or substances. The polyurethane resin constituent also functions as a nondegradable surface for the cleaning/storing solution.

In forming the outer membrane, a solution of 1.33% by weight of the Tecoflex TM resin product and 0.66% by weight of poly(ethylene glycol) in tetrahydrofuran is prepared. 5 Microliters of the solution is cast directly over the air-dried inner membrane 32, and is air-dried. Following drying, the outer membrane is washed with distilled water to remove the polyethylene glycol.

EXAMPLE 6

The structural integrity or mechanical strength of the electrode assembly formed in Example 5, above, is further enhanced and protected by placing a mesh 34 of inert, bio-compatible or blood-compatible material, such as polypropylene (e.g., having 100-micron pore size), directly over and on the outer membrane. This mesh may be capped with Mylar TM. The circular sheet of biocompatible mesh having a diameter, of 0.25 in., protects the underlying membrane structure (32 and 33) from damage that might result or occur during usage, cleaning, and the like.

The circular peripheral edge of the mesh 34 is maintained in place by frictionally positioning a Delrin TM (i.e., a linear polyoxymethylene-type acetal resin) retaining ring 35 snugly inside the annular ceramic sample cup or reservoir 30 after positioning the shaped, circular mesh material 34 in place. It has been found that a Delrin TM annular retention ring 35 with, for example, an outer diameter of 0.25 in., an inner diameter or 0.213 in., and a height of 0.05 to 0.1 is particularly useful. In forming sensor or electrode assemblies that provide the same reproducible results, the size and shape of the retention rings should be constant.

Delrin TM is a particularly suitable material for use in forming the retention ring because it is inert, electrically nonconductive and can be readily and accurately machined, and because it will swell slightly during usage to provide and retain a very secure, snug frictional fit in the sample cup without damaging other components of the electrode sensing or detector assembly. However, other suitable inert biocompatible materials may be used.

If desired, the mesh material and overlying retention ring may be formed as a single, integral unit as shown in FIGS. 5 and 6 and securely snap-fitted into the sample ring or reservoir.

EXAMPLE 7

(The Auxiliary Pair of Oxygen Generating Electrodes)

From the previously described glucose oxidase-catalyzed chemical of Reactions (1) and (1-A) which involve the catalytic conversion of blood glucose to gluconic acid and hydrogen peroxide, it can be seen that free oxygen must be available in the sample (reaction solution), for the glucose oxidase enzyme to work. In whole blood, most oxygen is bound to hemoglobin and is not available to participate in the glucose oxidase-catalyzed reaction. This has heretofore presented a major obstacle to the proper operation of various glucose sensor devices, particularly those used for measurements of glucose in whole blood.

An auxiliary pair of oxygen-generating electrodes 15 and 16 are provided to generate oxygen (by the electrolysis of water) in situ at the planar Pt electrode 15 whereupon the oxygen diffuses into the inner membrane 32. The auxiliary electrode assembly comprises two platinum electrodes 15 and 16 (one of the planar Pt electrodes described above, namely electrode 15, and overhanging Pt wire electrode 16) which, in use, are held at an electrical potential sufficiently great to result in the electrolysis of water present in the sample of whole blood, usually above about $+1.2$ volts. An applied voltage ($E_A$), for example, of from 3 to 4.5 volts result in satisfactory oxygen production when analyzing whole blood samples.

One may use a variety of different electrode patterns or arrangements for both determining the concentration of hydrogen peroxide and for generating oxygen. For example, as described above, one may use three electrodes (e.g., 2 Pt planar electrodes and 1 Ag/AgCl planar electrode) deposited on the flat or planar surface and a fourth Pt wire electrode which extends vertically downwardly into the insulative sample cup and contents thereof from above. The fourth electrode may also be planar and formed under the cavity of cup 30 in surface 11a.

When using a whole blood sample (placed in the sample cup), hydrogen is generated (at the vertically extending Pt wire 16 that extends into the sample cup) above the inner and outer membranes, and oxygen is generated (in the sample cup) at the surface of the deposited planar platinum electrode 15.

FIGS. 1 and 3 show the electrical circuitry that may be used in the electrochemical system. Referring to the circuitry shown in the upper portion of FIGS. 1 and 3, a constant applied voltage ($E_A$) of +0.8 volt is maintained to sense current (by ammeter A) generated by the oxidation of the hydrogen peroxide [see Reaction (2)] in a sample of predetermined volume. Connecting wire 18 connects the positive terminal of the battery to the planar Pt electrode 14, whereas the negative terminal is connected to the planar Ag/AgCl electrode 13 by means of connecting wire 17. Thus, the planar sensing electrode 14, at which hydrogen peroxide is oxidized, is positive and the Ag/AgCl reference electrode 13 is negative.

The circuitry shown at the lower portion of FIGS. 1 and 3 uses an applied voltage ($E_A$) of from +3 to 4.5 volts to provide for the electrolysis of water and thereby the generation of oxygen at the planar Pt electrode 15. Connecting wire 20 connects the negative terminal of the battery or potentiostat 26 to the overhanging Pt wire electrode 16, at which hydrogen is generated, and connecting wire 19 connects the positive terminal to the planar Pt electrode 15, at which oxygen is generated.

Although the immobilized enzyme, hydrogen peroxide-producing and sensing device and method described above concerns an in vitro hydrogen peroxide sensing system for enzymatically converting glucose (e.g., β-D-glucose) to gluconolactone (which undergoes rapid hydrolysis to form gluconic acid) and $H_2O_2$, and accurately and reproducibly determining glucose concentration, the invention also may be useful in minimally invasive in vivo sensing systems in which accurate and virtually instantaneous measurement of glucose concentration is desired.

Moreover, this invention may provide an important step towards the development of a safe and effective, internally inserted system, such as an artificial pancreas used in conjunction with controlled drug release means (e.g., controlled release of insulin). See, for example, U.S. Pat. 4,055,175 to Clemens et al., which concerns apparatus for controlling the concentration of glucose in the blood stream of a subject by the controlled supply of insulin to such subject dependent upon the particular concentration of glucose in the blood stream and the rate of change of the blood glucose concentration.

The enzyme immobilization technology involved in this invention has many different areas of application. For example, the first area of application, as described above, concerns biosensors in which hydrogen peroxide is an enzyme-induced or enzyme catalyzed reaction or conversion product. Numerous oxidase enzymes, for example, may be used to generate hydrogen peroxide from selected substrates or metabolites (in aqueous media) as an enzyme-catalyzed reaction or conversion product. Accordingly, "coupled" enzyme systems may be used in which a plurality of selected coacting enzymes are co-immobilized (in operative coacting proximity to, or in the operative coacting vicinity of quantitative hydrogen peroxide-sensing or detector electrode means) by being covalently bonded or bound to and within the permeable, poly(styrene-maleic anhydride) copolymer. In this way, the concentration of a given substrate or metabolite (in aqueous medium) may be determined based upon the level of hydrogen peroxide produced as a final or ultimate reaction or conversion product.

For example, the concentration of lactose substrate or metabolite in aqueous medium (e.g., milk) may be accomplished by using an immobilized enzyme electrode biosensor in which lactase and glucose oxidase enzymes are both covalently co-immobilized to an in the inner membrane. Enzymatic conversion of the lactose by the lactose enzyme produces glucose, which, in turn, can be enzymatically oxidized by glucose oxidase to catalytically yield hydrogen peroxide as a conversion product. The concentration of hydrogen peroxide, in turn, may be correlated to an consequently represent a direct and accurate measurement of lactose concentration in the aqueous medium (e.g., milk).

A second area of application relates to bioreactor technology wherein an immobilized enzyme is used to convert one chemical to another chemical in bulk fluid. This area of application could be useful for blood detoxification and treatment of disease states.

A third area of application relates to the immobilization of antibodies for immuno-diagnostic applications. In this particular area of use, immobilized antibodies would allow quantitation of proteins of interest.

A fourth area of application is as a monitoring device in fermentation systems, e.g., to monitor or measure glucose in a nutrient broth.

Accordingly, this invention has medical, or health or health care-related applications or uses (e.g., use in a hospital or clinic, at a doctor's office, or in the home), as well as industrial applications (e.g., in controlling fermentation and food processing operations).

The foregoing detailed description has been given for clearness of understanding only, and the forms of the inventions shown and described therein are to be considered as illustrative, and no unnecessary limitations should be understood therefrom, as modifications or variations will be obvious to those skilled in the art without departure from the spirit of the inventions or the scope of the appended claims, which follow.

What is claimed is:

1. An electrochemical detector device for determining the concentration of a substrate in an aqueous sample which comprises:
    (a) a base surface;
    (b) a set of planar electrodes affixed to said base surface;
    (c) a resilient permeable inner membrane in substantially interfacial contact with said planar electrodes, said inner membrane being comprised of a polyvinyl acetate and polyethylene glycol modified poly(styrene-maleic anhydride) polymer and having an enzyme specific to said substrate distributed and immobilized therein by covalently bonding the anhydride group of a poly(styrene-maleic anhydride) copolymer to amine groups of the said enzyme, the enzyme being adapted to catalytically convert the substrate to a electrochemically measurable derivative;
(d) a permeable biocompatible, blood compatible aliphatic polyurethane/butadiene resin polymeric outer membrane having a top and bottom surface, the bottom surface in substantially interfacial contact with said inner membrane, said outer membrane being adapted to restrict the passage of electrochemically interfering substances to said inner membrane but permeable to the substrate to be attached;
(e) a housing affixed to said base surface, containing the inner and outer membranes and underlying electrodes, said housing adapted to contain an aqueous sample of the substrate to be measured;
(f) a means for measuring current generated by a redox reaction of the electrochemically measurable derivative formed by action of the enzyme on the substrate to be measured.

2. An electrochemical detector device for determining the concentration of a substrate in an aqueous sample which comprises:
(a) a base surface;
(b) a set of planar electrodes affixed to said base surface;
(c) a resilient permeable inner membrane in substantially interfacial contact with said planar electrodes, said inner membrane being comprised of a polyvinyl acetate and polyethylene glycol modified poly(styrene-maleic anhydride) polymer and having an enzyme specific to said substrate distributed and immobilized therein by covalently bonding the anhydride group of a poly(styrene-maleic anhydride) copolymer to amine groups of the said enzyme, the enzyme being adapted to catalytically convert the substrate to an electrochemically measurable derivative;
(d) a permeable blood compatible, biocompatible aliphatic polyurethane/butadiene resin polymer outer membrane having a top and a bottom surface, the bottom surface in substantially interfacial contact with said inner membrane, said outer membrane being adapted to restrict the passage of electrochemically interfering substances to said inner membrane but permeable to the substrate to be detected;
(e) a housing affixed to said base surface, containing the inner and outer membranes and underlying electrodes, said housing adapted to contain an aqueous sample of the substrate to be measured;
(f) an electrode for the generation of oxygen by the electrolysis of water to provide a source of oxygen to the inner membrane;
(g) a means for measuring current generated by redox reaction of the electrochemically measurable derivative of the substrate at a planar positive electrode.

3. The electrochemical concentration detector device of claim 2 wherein said electrodes include a planar Ag/AgCl reference electrode and planar platinum electrode for sensing and signaling the concentration of the derivative of the substrate enzymatically formed in the detector device.

4. The electrochemical concentration detector device of claim 2 wherein the electrode configuration of the planar electrodes is a semi-circle.

5. The electrochemical concentration detector device of claim 2, wherein said planar electrode material is formed on said base surface by sputtering.

6. The electrochemical concentration detector device of claim 2, wherein said planar electrodes are formed on said base surface by silk screening.

7. The electrochemical concentration detector device of claim 2, wherein at least one of said planar electrodes is formed of a mixture of carbon and platinum.

8. An electrochemical concentration detector device of claim 2, wherein the immobilized enzyme is glucose oxidase.

9. The electrochemical concentration detector device of claim 2 wherein said inner membrane is formed in admixture with polyethylene glycol and said inner membrane is eluted to remove polyethylene glycol to provide an inner membrane of the requisite porosity.

10. The electrochemical concentration detector device of claim 2 wherein the enzyme is immobilized by dispersing an aqueous solution of the enzyme in an organic solvent solution of the polymer, under time and temperature conditions to form a chemical bond between enzyme and polymer.

11. The electrochemical concentration detector device of claim 2 wherein said inner membrane is deposited by silk screening a layer of solvent solution of said resin over the planar electrodes.

12. The electrochemical concentration detector device of claim 2, wherein said inner membrane is proximally cast on said set of planar electrodes.

13. The electrochemical concentration detector device of claim 2, wherein said device includes an inert, biocompatible, mesh material maintained directly over the top surface of said outer membrane.

14. The electrochemical concentration detector device of claim 13 wherein said mesh material is polypropylene.

15. An operative membrane composite, consisting of an inner and outer membrane, adapted for use in an electrochemical enzymatic substrate concentration detector device which comprises:
(a) a resilient inner membrane formed from a permeable, polyvinyl acetate-polyethylene glycol modified poly(styrene-maleic anhydride) polymer having immobilized therein at least one oxidation/reduction enzyme containing amine groups, said at least one enzyme being immobilized by covalently bonding the anhydride group of a poly(styrene-maleic anhydride) copolymers to amine groups of the enzyme, said immobilized enzyme upon contact with a selected substrate in aqueous medium catalytically causes said substrate to undergo conversion in situ to yield $H_2O_2$, and in interfacial contact therewith;
(b) a permeable aliphatic polyurethane/butadiene resin polymeric outer membrane having a top and bottom surface, said outer membrane providing a biocompatible, blood compatible interface with fluids bearing the substrate and is fluid communicatible with said inner membrane, through pores sized to restrict the passage of interfering electrochemically substances in the sample into said inner membrane, but permeable to the substrate to be detected.

16. The operative membrane composite of claim 15 which is protected by a biocompatible, polypropylene mesh adjacent to the top suface of said outer membrane.

17. An electrochemical concentration detector device for determining the concentration of glucose in an aqueous sample which comprises:
  (a) a base surface;
  (b) a set of planar electrodes affixed to said base surface;
  (c) a resilient permeable inner membrane in substantially interfacial contact with said planar electrodes, said inner membrane being comprised of a polyvinyl acetate-polyethylene glycol modified poly(styrene-maleic anhydride) polymer and having a glucose oxidase enzyme immobilized therein covalently bonding the anhydride group of a poly(styrene-maleic anhydride) copolymer to amine groups in said enzyme adapted to catalytically convert glucose to hydrogen peroxide;
  (d) a permeable biocompatible, blood compatible outer membrane having a top and a bottom surface, the bottom surface in substantially interfacial contact with said inner membrane, said outer membrane being adapted to limit the passage of interfering substances to said inner membrane;
  (e) a housing affixed to said base surface, containing the inner and outer membranes, and underlying electrodes, said housing adapted to contain a fluid sample containing the substrate to be measured;
  (f) an electrode pair for the generation of oxygen by the electrolysis of water to provide oxygen to the inner membrane;
  (g) a means for measuring the current generated by a redox reaction of the hydrogen peroxide at a planar positive electrode of a second electrode pair.

18. The electrochemical concentration detector device of claim 17 wherein said electrodes include a planar Ag/AgCl reference electrode and planar platinum electrode for sensing and signaling the concentration of hydrogen peroxide enzymatically formed in the detector device.

19. An electrochemical concentration detector device of claim 17 wherein the electrode configuration of the planar electrodes is a semi-circle.

20. The electrochemical concentration detector device of claim 17, wherein said planar electrode material is formed on said base surface by sputtering.

21. The electrochemical concentration detector device of claim 17 wherein the planar electrodes are formed of a mixture of carbon and platinum.

22. The electrochemical concentration detector device of claim 17 wherein said inner membrane is formed initially as an admixture with polyethylene glycol and said inner membrane is then eluted to remove said polyethylene glycol to provide an inner membrane of the requisite porosity.

23. The electrochemical concentration detector device of claim 17 wherein the enzyme is immobilized by dispersing an aqueous solution of the enzyme in an organic solvent solution of the polymer, under time and temperature conditions to form a chemical bond between the enzyme and polymer.

24. The electrochemical concentration detector device of claim 17 wherein said inner member is deposited by silk screening in a layer of solvent solution of said resin over the planar electrodes.

25. The electrochemical concentration detector device of claim wherein said outer membrane has pores sized to substantially exclude components of the sample, other than the substrate, to the inner membrane.

26. The electrochemical concentration detector device of claim 25 wherein said outer membrane is formed of polyurethane resin.

27. The electrochemical concentration detector device of claim 17, wherein said device includes an inert, biocompatible, mesh material maintained directed over the top surface of said outer membrane.

28. The electrochemical detector device of claim 27 wherein said mesh material is polypropylene.

29. An operative membrane composite adapted for use in an electrochemical glucose concentration detector device which comprises:
  (a) a resilient inner membrane of permeable, polyvinyl acetate-polyethylene glycol modified poly(styrene-maleic anhydride) polymer having glucose oxidase immobilized therein by covalently bonding the anhydride group of a poly(styrene-maleic anhydride) copolymer to amine groups of the said glucose oxidase, said immobilized enzyme upon contact with a glucose bearing colution catalytically causes said glucose to undergo conversion to yield $H_2O_2$ and in interfacial contact therewith; and
  (b) a permeable aliphatic polyurethane/butadiene polymers polymeric outer membrane having a top and bottom surface, said outer membrane providing a biocompatible and blood compatible interface with fluids bearing the glucose and is fluid communicatible with said inner membrane, through pores sized to restrict the passage of interfering electrochemically substances into said inner membrane but permeable to glucose.

30. The operative membrane composite of claim 29 which is protected by a biocompatible, blood compatible mesh of polypropylene adjacent to the top surface of said outer membrane.

* * * * *

UNITED STATES PATENT AND TRADEMARK OFFICE
CERTIFICATE OF CORRECTION

PATENT NO. : 4,795,542

DATED : January 3, 1989

INVENTOR(S) : Ross, et al

It is certified that error appears in the above-identified patent and that said Letters Patent is hereby corrected as shown below:

Column 8, line 29, "The" should be --This--.

Claim 25, Column 20, line 15, after the word "claim", insert --17--.

Claim 29, Column 20, line 37, after the word "bearing", change the word "colution" to --solution--.

Signed and Sealed this

Seventeenth Day of March, 1992

*Attest:*

HARRY F. MANBECK, JR.

*Attesting Officer*      *Commissioner of Patents and Trademarks*